US010852252B2

(12) United States Patent
Schlemm

(10) Patent No.: US 10,852,252 B2
(45) Date of Patent: Dec. 1, 2020

(54) DEVICE AND METHOD FOR MEASURING ABSORBENT HYGIENE PRODUCTS

(71) Applicant: TEWS Elektronik GmbH & Co. KG, Hamburg (DE)

(72) Inventor: Udo Schlemm, Hamburg (DE)

(73) Assignee: TEWS Elektronik GmbH & Co. KG, Hamburg (DE)

( * ) Notice: Subject to any disclaimer, the term of this patent is extended or adjusted under 35 U.S.C. 154(b) by 5 days.

(21) Appl. No.: 16/322,537

(22) PCT Filed: Aug. 1, 2017

(86) PCT No.: PCT/EP2017/069459
§ 371 (c)(1),
(2) Date: Feb. 1, 2019

(87) PCT Pub. No.: WO2018/024735
PCT Pub. Date: Feb. 8, 2018

(65) Prior Publication Data
US 2020/0191729 A1 Jun. 18, 2020

(30) Foreign Application Priority Data
Aug. 2, 2016 (DE) .......................... 10 2016 114 287

(51) Int. Cl.
G01R 27/04 (2006.01)
G01R 27/32 (2006.01)
(Continued)

(52) U.S. Cl.
CPC ....... G01N 22/04 (2013.01); A61F 13/15585 (2013.01); G01N 22/00 (2013.01);
(Continued)

(58) Field of Classification Search
CPC .... G01N 22/04; G01N 22/00; G01N 33/2823; G01N 33/346; G01R 27/2658; G01R 1/24; G01R 23/20; G01R 27/04
(Continued)

(56) References Cited

U.S. PATENT DOCUMENTS

2005/0179443 A1* 8/2005 Peters .................. D01G 31/006
324/636
2008/0211514 A1* 9/2008 Kaufmann ............. G01N 22/04
324/601
(Continued)

FOREIGN PATENT DOCUMENTS

EP 1327876 A1 7/2003
EP 1933132 A2 6/2008
(Continued)

OTHER PUBLICATIONS

PCT/EP2017/069459 English translation of International Search Report dated Nov. 9, 2017, 2 pages.
(Continued)

Primary Examiner — Raul J Rios Russo
(74) Attorney, Agent, or Firm — Barclay Damon LLP

(57) ABSTRACT

A device for measuring absorbent bodies that are spaced from each other on a continuous web comprises at least two microwave resonators configured to measure values of a shift of a resonance frequency and a spreading of a resonance frequency. The continuous web moves through the at least two microwave resonators and the at least two microwave resonators are positioned at an offset with respect to each other in the transverse and transport direction relative to a direction of transport of the continuous web in order to measure the entire width of the continuous web. At least one of a moisture and a density of the absorbent bodies is determined using the at least two microwave resonators to continuously determine the values of the shift of the resonance frequency and the spreading of the resonance frequency.

12 Claims, 3 Drawing Sheets

(51) Int. Cl.
*G01N 22/04* (2006.01)
*A61F 13/15* (2006.01)
*G01N 22/00* (2006.01)
*G01N 33/28* (2006.01)
*G01N 33/34* (2006.01)
*G01R 27/26* (2006.01)
*G01R 1/24* (2006.01)
*A61F 13/84* (2006.01)
*G01R 23/20* (2006.01)

(52) U.S. Cl.
CPC ....... *G01N 33/2823* (2013.01); *G01N 33/346* (2013.01); *G01R 1/24* (2013.01); *G01R 27/2658* (2013.01); *A61F 2013/8491* (2013.01); *G01R 23/20* (2013.01); *G01R 27/04* (2013.01)

(58) Field of Classification Search
USPC .......... 324/76.11–76.83, 459, 600, 629, 633, 324/634, 640, 643, 652, 655, 658, 675, 324/694, 696, 708
See application file for complete search history.

(56) References Cited

U.S. PATENT DOCUMENTS

| | | | |
|---|---|---|---|
| 2010/0141270 A1* | 6/2010 | Kaufmann | D21G 9/0009 324/634 |
| 2010/0176818 A1* | 7/2010 | Herrmann | G01N 22/04 324/640 |
| 2011/0093212 A1* | 4/2011 | Herrmann | G01N 22/04 702/23 |
| 2016/0051414 A1 | 2/2016 | Piantoni et al. | |
| 2019/0175421 A1* | 6/2019 | Schlemm | A61F 13/15203 |

FOREIGN PATENT DOCUMENTS

| | | |
|---|---|---|
| EP | 2207027 A2 | 7/2010 |
| WO | 2014/170796 A1 | 10/2014 |

OTHER PUBLICATIONS

PCT/EP2017/069459; International Filing Date Aug. 1, 2017; English translation of International Preliminary Report on Patentability; dated Feb. 14, 2019 (20 pages).

* cited by examiner

DEVICE AND METHOD FOR MEASURING ABSORBENT HYGIENE PRODUCTS

CROSS REFERENCE TO RELATED INVENTION

This application is a national stage application pursuant to 35 U.S.C. § 371 of International Application No. PCT/EP2017/069459, filed on Aug. 1, 2017, which claims priority to, and benefit of, German Patent Application No. 10 2016 114 287.5, filed Aug. 2, 2016, the entire contents of which are hereby incorporated by reference.

BACKGROUND

The present invention relates to a device and method for measuring absorbent hygiene products, in particular for measuring absorbent hygiene products during their production during which absorbent bodies are placed at a distance from each other on a continuous web.

A method is disclosed in EP 1 327 876 B1 for recognizing foreign bodies in continuous mass flows consisting of fibrous, strand-shaped or bulk good material with the assistance of a microwave resonator. The mass flow is guided through a field of the microwave resonator during which the change (A) of the resonator frequency caused by the material and the change (B) in the width of the resonance curve of the microwave resonator are determined. The ratio of the changes is compared with corresponding averages, and the presence of a foreign body is reported when the ratio of the changes deviates from the average by more than one given value.

A method is known from WO 2014/170796 A1 for producing absorbent hygiene products. The absorbent hygiene products, such as in the form of a diaper, has an absorbent pad as an absorbent body that also possesses one or more absorbent materials. The absorbent pads are placed along a web of a permeable material, wherein a microwave resonator is provided that creates a weight profile or agency profile of the least one absorbent material. Different positions on the diaper machine are proposed for the measuring position of the microwave resonator. Particular problems in the evaluation of the data result from the fact that, in the production of diapers, the diaper cores are placed with a slight spacing on the continuous web of a polyethylene outer sleeve and permeable cover layer. In this sense, there is no empty mode of the microwave resonator that could be used for a comparison of empty values.

BRIEF SUMMARY OF THE INVENTION

The object of the invention is to provide a device and a method for measuring absorbent hygiene products with the assistance of a microwave resonator.

The device according to the invention serves to measure absorbent hygiene products, wherein absorbent bodies that are spaced from each other are placed on a continuous web in the method. The moisture and/or density of the absorbent bodies are ascertained in two or more microwave resonators with the assistance of a shift of the resonance frequency (A) and a spreading of the resonance frequency (B). The web is transported through the microwave resonators, and two microwave values are continuously determined.

Particularly in the production of absorbent hygiene products, in particular diapers, the problem can occur that the web which is to be measured continuously is too wide for the microwave resonator relative to the direction of transport. This problem is solved by the use of at least two microwave resonators that are arranged offset from each other in the transverse and transport direction relative to a direction of transport of the web in order to measure the web over its entire width. Relative to the direction of transport, the two or more microwave resonators are arranged offset from each other in the transverse direction in order to be able to measure the web over its entire width. In this case, the microwave resonators that are transversely offset from each other must also be arranged offset from each other in the transport direction since they generally possess a homogeneous field distribution in a central region. By offsetting the microwave resonators in the longitudinal direction, they can be arranged overlapping each other so that the web is measured with a homogeneous field distribution over its entire width.

In a preferred further development of the measuring method according to the invention, each microwave resonator forms an average of its measured values in the transverse direction relative to the direction of transport of the web. The averaged measured values of the plurality of microwave resonators are corrected by an offset of the microwave resonators in the direction of transport in order to determine an overall average for the entire width of the web. In correcting by the offset of the microwave resonators, it is taken into account that the averaged measured values must be added to each other with a temporal offset in order to obtain an average for the overall width of the web due to the spatial offset of the microwave resonators to each other and the transport speed of the web.

In a preferred embodiment, each of the microwave resonators possesses a measuring range with a homogeneous field distribution, wherein the plurality of microwave resonators is positioned transverse to the transport direction such that the overall web is covered by measuring ranges with a homogeneous field distribution. A homogeneous field distribution helps achieve reliable and precise measuring results. Given the homogeneous field distribution, it is also possible to average the recorded measured values in the transverse direction of the web. A plurality of microwave resonators are arranged sequentially such that the width of the web is entirely covered with a measuring range with a homogeneous field distribution.

In the method according to the invention, at least two microwave resonators are continuously used for measuring, wherein the microwave resonators are arranged offset from each other in the transverse and transport direction relative to the direction of transport. The entire width of the web is measured by the at least two microwave resonators.

Preferably, each of the microwave resonators averages its measured values in the transverse direction so that the average measured values in the transverse direction can be corrected by an offset of the microwave resonators in the transport direction. It is ensured in this manner that the web is always evaluated in a measuring range extending over the entire width.

To determine the mass and/or moisture of the absorbent bodies, an approach is selected that determines the totaled measured values of the microwave variables. In order to be independent of the transport speed, the totaled measured values of the two measured variables are preferably divided by the number of summands. The averaged sum value determined in this manner only depends on the length of the absorbent body in the transport direction, and not, however, on the transport speed.

In a preferred embodiment of the method according to the invention, the mass of an absorbent body is determined by adding the measured values. In this case, preferably each individual measured value is added and compared with the overall weight to be determined. The summed measured values are divided by the number of their summands.

BRIEF DESCRIPTION OF THE DRAWINGS

The method according to the invention will be further explained below with reference to an exemplary embodiment. In the following.

DETAILED DESCRIPTION OF THE INVENTION

Figure 1:
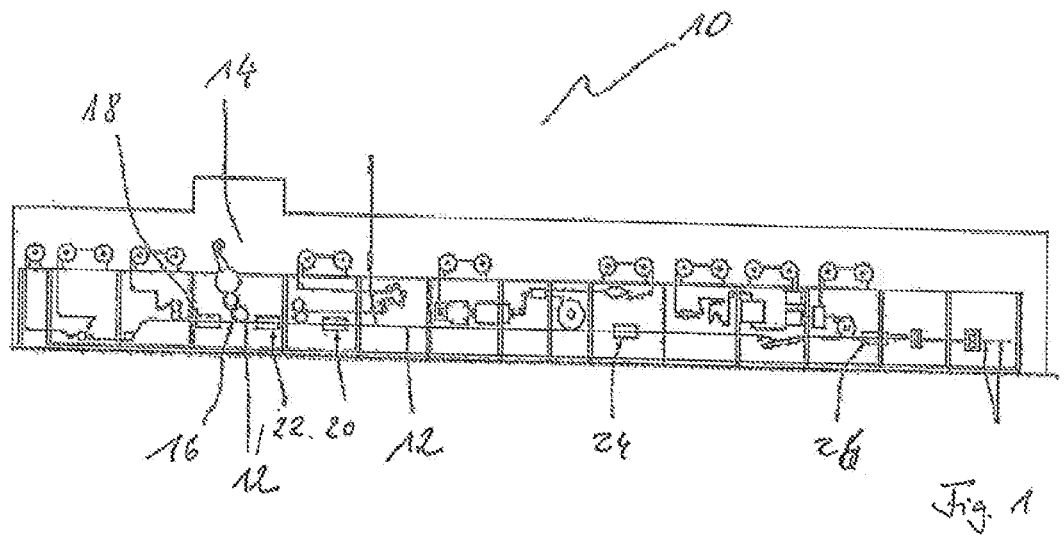
FIG. 1 shows the basic design of a diaper machine and possible positions of a microwave resonator.

FIG. 1 shows a schematic view of the overall design of a diaper machine 10. The machine 10 possesses a continuous web 12 consisting of a polyethylene outer sleeve that continuously runs through the machine at a high speed in order to produce a diaper. At periodic intervals, diaper cores are applied in a section 14 of the machine. The applied diaper cores consist of absorbent pads and are positioned on the web 12 that is passing through. The schematically portrayed detection apparatuses 18 and 20 are conventionally operating detection apparatuses that for example optically monitor the web and the applied diaper core. A microwave resonator 22, 24, 26 is positioned along the production process in order to repeatedly measure weight and moisture of the diapers and the web 12. Depending on the position of the microwave resonator along the web 12, the microwave measured values for the weight and moisture can be measured and monitored in various stages of production.

A single-use or disposable diaper consists of an outer sleeve of polyethylene (PE) and an absorbent body that generally consists of a cellulose material which is enriched with a super absorber (polymer salts). The amount of liquid can be bound by the absorbent body by the multiple of its own volume, and the liquid can be held even upon exertion of pressure.

In the production of diapers, an endless web 12 of the polyethylene outer sleeve is provided at periodic intervals in the diaper machine 10 with a permeable cover layer with the absorbent bodies. In this case, the absorbent bodies consist of a mixture of cellulose and powdered super absorber (SAP=superabsorbent polymer material).

For quality control in production, it is desirable to measure the overall weight and/or density profile of the diaper cores using microwave resonators. A series of suggestions for positioning the microwave resonators in a diaper machine is known from WO 2014/170796 A1. An approach for evaluating the measured values in order to achieve reliable and precise results is not known.

With a microwave resonator, a shift in the resonance frequency A and a widening of the resonance curve B is measured as a consequence of the dielectric properties of the specimen to be investigated. The measured values are formed as a difference between the values of the filled and empty resonator. The resonance frequency shift A in Hz is:

$$A = f_0 - f_m,$$

wherein $f_0$ indicates the resonance frequency of the empty resonator in Hz, and $f_m$ indicates the resonance frequency of the filled resonator in Hz. The increase in the peak width at half maximum of the resonance B in Hz is employed for the widening of the resonance curve. The following applies:

$$B = w_m - w_0,$$

wherein $w_0$ designates the peak width at half maximum of the resonance of the empty resonator in Hz, and $w_m$ designates the peak width at half maximum of the resonance of the filled resonator in Hz.

From the above approach, it is clear that information on the resonance parameters of the empty resonator belongs to each measurement. The empty resonance values change as the temperature changes and as the resonator becomes soiled. In order to suppress the influence of the empty resonance values on the measured values, the following measures are taken in practice:

In laboratory measurements, there is a measurement of the current empty resonance values for each recorded measured value.

In process measurements in which the empty resonance values can only be measured rarely, the sensor is encapsulated and regulated to a constant temperature. In addition, the sensor is regularly cleaned with compressed air.

In the case of portioned units that are embedded in an endless, non-metal support material, the case is described as a procedure in DE 10 2009 004 457 A1 in which the distances of the portioned units in the support material is greater than the diameter of the employed microwave resonator. This ensures that the sensor only detects the support material between the portioned units. The known evaluation requires only the support material, i.e., the web without the portioned unit, to be located within the measuring range at periodic intervals. This means that the spacing of the portioned unit must be greater than the employed measuring field.

When used in the diaper machine, the spacing between two diaper cores is frequently smaller than the diameter of the sensor. Accordingly, at no time is only the support material by itself located in the sensor. This means that the sensor always contains measuring signals from the diaper package to a certain extent. Nonetheless, it was found that periodic signal minima arise between the cores along the web when diaper cores are used. The invention is based on the insight that when detecting these minima, the signals can be calculated based on the difference between the measured values A and B and the measured values of the respective local minima Amin and Bmin instead of an empty adjustment. It is accordingly possible to compensate for all temperature influences on the sensor as well as signal fluctuations from soiling without an empty adjustment (as is known from the prior art).

The evaluation algorithm according to the invention for the microwave resonators is especially suitable for spacings between diaper cores that are less than the measuring range of the microwave resonators. Of course, the evaluation according to the invention using the local minima values and their moving average can also be used when the spacings between the diaper cores is greater than the employed measuring field due to a particular configuration of the diaper machine. The method according to the invention can accordingly be used universally independent of the spacing of the diaper cores.

Another advantage when using minimum detection is that, in the known evaluation method according to the prior art, the diaper sheet must be moved into a predefined position relative to the sensor when the measuring process starts i.e., the region between two diaper cores must for example be located in the sensor. In this position, the first empty adjustment is performed that is then the basis for the following periodic empty adjustments. This procedure is discarded when using minimum detection since sensor empty adjustment is not needed when using this method.

The method that is known from EP 1 467 191 A1 for measuring capsules/tablets also always requires the conveyor belt to be without capsules or tablets to measure an empty adjustment between two tablets to be measured.

Figure 3:
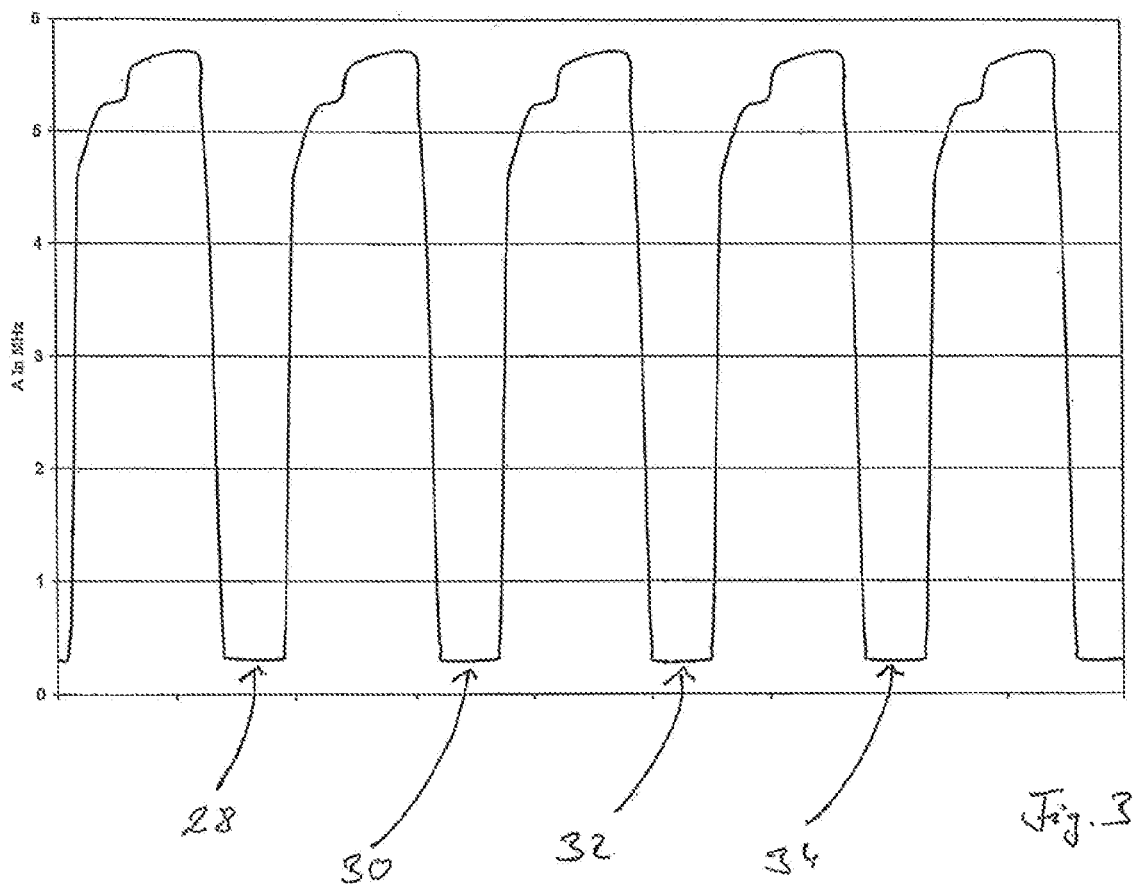
FIG. 3 shows signals of a diaper sheet where the spacing of the diaper cores is greater than the diaper diameter.

FIG. 3 shows the signal characteristic of the resonance frequency shift A in which the distance between two diaper cores in the transport direction is greater than the extent of the measuring range in the transport direction. In this measuring situation, minimum values 28, 30, 32, 34 occur at periodic intervals between the diaper cores in which only the web 12 is located within the measuring range. It is clearly discernible that the measured values for a configuration in which the web passes through the microwave resonator without a diaper core are nearly constant and accordingly change appropriately for an empty adjustment of the signal values.

Figure 2:
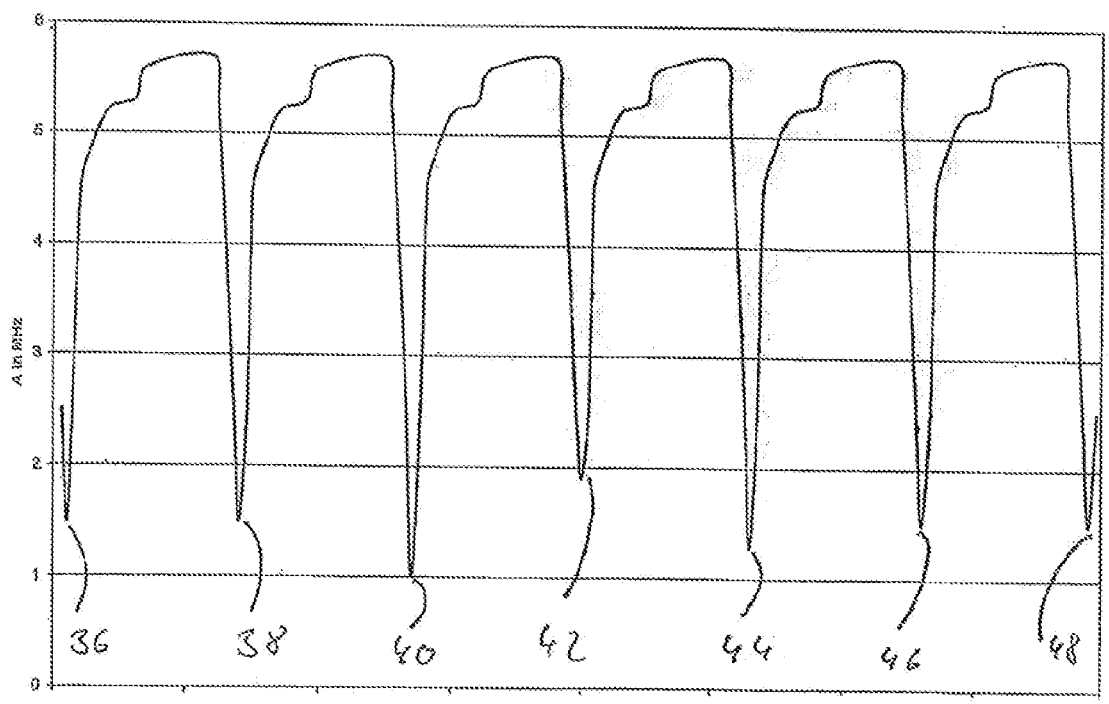
FIG. 2 shows signals of a diaper sheet where the spacing of the diaper cores is less than a sensor diameter.

The behavior of the measured variables, in particular in the minimum range, changes significantly in FIG. 2. In this case, the distance between two diaper cores is less than the measuring range of a microwave resonator. In FIG. 2, it is discernible that the local minimum values 36 to 48 fluctuate significantly from each other. Accordingly, for example the local minimum values 40 and 42 differ from each other nearly by 1 MHz. The extent of the fluctuation becomes clear when it is considered here that the fluctuation is nearly 100% of the local minimum 40.

The minimum values portrayed in FIG. 2 fluctuate so strongly due to the measuring setup that a reliable evaluation by a simple empty adjustment, or respectively subtracting the signal values, only yields a very imprecise measured value. A measurement of the minima at a fixed machine cycle is also not possible.

In order to minimize the influence of the individually occurring variations in the minimum values 36-48, it is proposed according to the invention to form a moving average over the signal minima and use them to form the difference. A moving average $A_{min\_AV}$ is therefore used to form the difference while forming a signal. The moving average is:

$$A_{min\_AV} = (A_{min\_1} + A_{min\_2} + \ldots + A_{min\_N})/N$$

wherein $\{A_{min\_i}\}$ designates the last local minima for the resonance frequency shift A. The moving average formed in this manner is used to form the difference so that the following value is used as measured variable A:

$$A = A_{\_core} - A_{min\_AV},$$

wherein $A_{\_core}$ is the measured A value for the diaper core. The same procedure is used for the B values.

In addition to the above-described arithmetic averaging for the A values, other types of averaging can also be used. In particular, it may also be of interest to use weighted averages where measured values that lie further in the past are given less weight in the measurement than minimum values just recorded.

The measured variables A, B determined with the assistance of the microwave resonators can be evaluated in different ways. Since super absorbers are used as a very hydrophilic material in the production of diapers, in particular the determination of the moisture, or respectively a moisture profile, is also particularly relevant for the diaper core. It is also relevant to determine the overall mass and a density profile for the diapers from the measured variables A, B.

The overall mass of the diaper cores is obtained by adding or integrating the measuring signals A, B over the respective diaper core. If the integral value is divided by the number of individual measurements M, the mass of the diaper core can thus be determined using the following calibration equation:

$$\text{Mass}_{diapercore} = a_1 \cdot \text{Int}(A)/M + a_2 \cdot \text{Int}(B)/M + a_3,$$

where the function "Int" stands for the integral or the sum of the values, and M describes the number of the measurement over the diaper core. The parameters $a_1$, $a_2$ and $a_3$ can be established when calibrating for the subsequent procedure. The moisture contained in the diaper can correspondingly be obtained by evaluating the moisture values with B/A. The parameters $a_1$, $a_2$, $a_3$ are dependent on the length of the diaper core, and independent of the transport speed.

In determining the overall mass of the diaper cores, it is in principle also possible to determine the mass depending on the value of the integral of the microwave measured values. This is expressed as follows:

$$\text{Mass}' = a_1' \cdot \text{Int}(A) + a_2' \cdot \text{Int}(B) + a_3',$$

where $a_1'$, $a_2'$ and $a_3'$ are parameters that are determined by a calibration. It is interesting in this case that the calibration can only be performed for one production speed since the values of the integrals depends on the speed. It is theoretically possible to include the speed with which the diaper is moved through the sensor in the calibration equation.

In practice, it has been revealed that the approach of considering the average of the integrals (Int(A)/M, Int(B)/M) yields the more precise values since the average of the integrals only depends on the length of the diaper cores which fluctuates very little.

Another feature of measuring with microwave resonators for absorbent hygiene products is that the web-shaped material may possess a large width in certain circumstances. Preferably, wide fork-type sensors are used to measure web-shaped material as for example known in the textile field from EP 1 316 630 B1. These fork-type sensors basically consist of a cylinder divided in two along its longitudinal axis through which the web-shaped material is guided. Fork-type sensors possess great field homogeneity in the direction of the cylinder, i.e., perpendicular to the transport direction of the web to be measured. It is therefore possible to precisely measure density and mass profiles transverse to the direction of movement, wherein the sensor measures a strip in the direction of movement in an integrating manner.

To achieve the aforementioned field homogeneity, the so-called basic mode E010 is operated in a fork-type sensor. If d is designated as the diameter of a cylindrical fork-type sensor and l as its length, it accordingly holds true for $d/l \to 0$ that the resonance frequency $f_0$ of mode E011 increasingly approaches the basic mode E010. Given this approach, the basic mode is no longer useable for measuring in practice since effects and influences from the E011 mode which is also instigated are always manifested. Accordingly, the length of fork-type sensors is limited for physical reasons and cannot be scaled or lengthened arbitrarily. For frequencies of 2-3 GHz for example, fork-type sensors can be used at most up to a length of about 20 cm. Such a measuring width may be too small for hygiene products such as diapers for adults.

Figure 4:
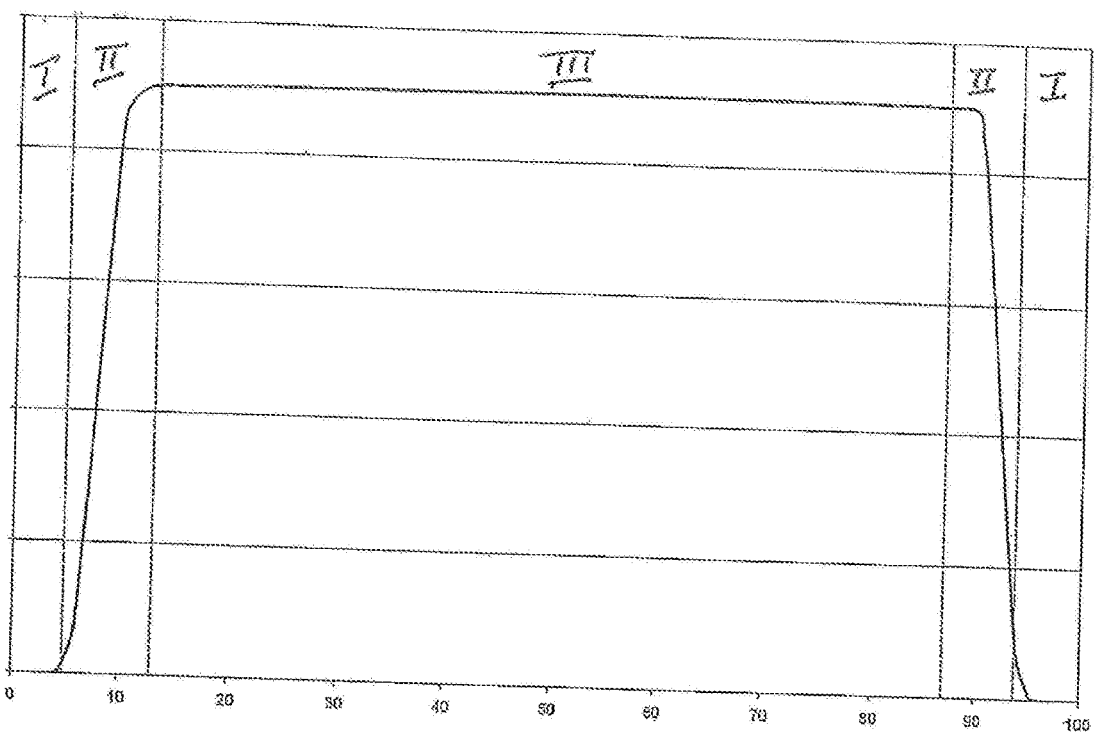
FIG. 4 shows a schematic view of the field distribution in a fork resonator in a longitudinal direction.

FIG. 4 shows the field strength distribution in a fork-type sensor in the direction of the cylinder axis. Three zones can be distinguished:

I. A field strength range outside of the resonance space in which the field strength decreases exponentially.

II. An inhomogeneous field strength range at the floor and cover of the cylinder structure, and III. a homogeneous field strength range that is particularly well-suited for measuring mass and density.

Figure 5:
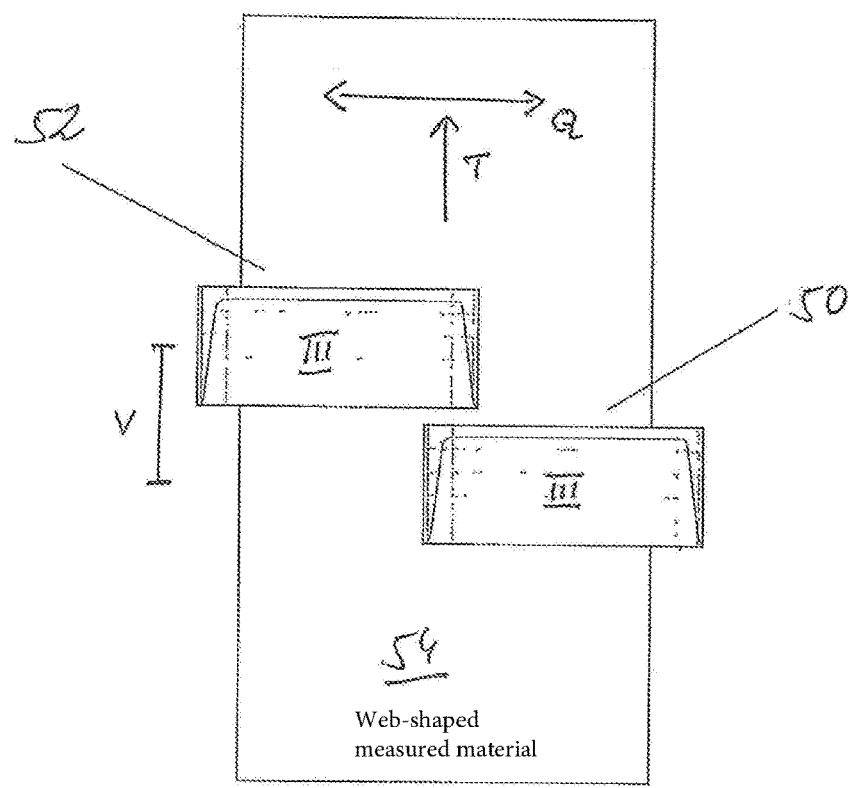
FIG. 5 shows an arrangement of two forked sensors for a web-shaped measured material.

An offset arrangement of the fork resonators 50, 52 portrayed in FIG. 5 makes it possible to detect the entire web-shaped measured material 54 with the homogeneous field ranges III of the two fork resonators 50, 52. The homogeneous measuring ranges III of the fork resonators 50, 52 are offset relative to each other in the transverse direction Q and in the transport direction T.

The offset V in the transport direction arising between the fork resonators 50 and 52 can be taken into consideration by a temporal offset when evaluating the measuring signals. When using the sensors 50, 52, the mass per length unit is determined by the following four measured values:

$A_1, B_1, A_2, B_2,$ wherein A designates the resonance frequency shift and B the spread of the resonance, and the indices refer to the resonators 50 and 52.

The mass per length unit m in for example g/cm can be determined by the following relationship:

$$m = a_1 \cdot A_1 + a_2 \cdot A_2 + a_3 \cdot B_1 + a_4 \cdot B_2 + a_5,$$

where $a_i$ designates the calibration coefficients.

At the same time, the moisture of the measured material u can be measured in %. The quotient of the microwave measured values is used for density-independent moisture measurement. As is usual, the following is defined: $\Phi = B/A$ or $\Phi = \arctan(B/A)$. The moisture of the measured material u in % is determined using the microwave moisture values from the two resonators. Let $\Phi_1 = \arctan(B_1/A_1)$ and $\Phi_2 = \arctan(B_2/A_2)$ for the microwave resonators 50, 52. The determined moisture value u is then:

$$u = b_1 \cdot \Phi_1 + b_2 \cdot \Phi_2 + b_3,$$

where $b_1$ designates the calibration coefficients.

Due to production tolerances of the fork-type sensors, the measurements in both fork resonators yield different measured values for measured variables A and B for the same product. By test measurements of a homogeneous material, the two measured variables of the resonators 50, 52 can be set in relation to each other. An offset between the resonators can be omitted for a homogeneous material. One approach for evaluating measured signals can therefore be:

$$A_1 = c_1 \cdot A_2,$$

$$B_1 = c_2 \cdot B_2,$$

where $c_1$ and $c_2$ are predetermined coefficients. The advantage of previously setting the measured variables of the two microwave resonators in a constant relationship $c_1$, $c_2$ with each other is that fewer calibration coefficients $a_i$ must be determined for the mass and moisture values.

In principle, the above-described arrangement of the microwave resonators 50, 52 can also be expanded to more than two microwave resonators in order to measure the web to be measured with a field distribution as homogeneous as possible.

The invention claimed is:

1. A device for measuring absorbent bodies that are spaced from each other on a continuous web, the device comprising:
   at least two microwave resonators configured to measure values of a shift of a resonance frequency and a spreading of a resonance frequency, wherein the continuous web moves through the at least two microwave resonators and the at least two microwave resonators are positioned at an offset with respect to each other in the transverse and transport direction relative to a direction of transport of the continuous web in order to measure a width of the continuous web,
   wherein at least one of a moisture and a density of the absorbent bodies is determined using the at least two microwave resonators to continuously determine the measured values of the shift of the resonance frequency and the spreading of the resonance frequency, and
   wherein each of the at least two microwave resonators has a measuring range with a homogeneous field distribution, and wherein the at least two microwave resonators are positioned transverse to the transport direction such that the continuous web is covered by measuring ranges with a homogeneous field distribution.

2. The device according to claim 1, wherein the measured values of the shift of the resonance frequency and the spreading of the resonance frequency are corrected by an offset of the at least two microwave resonators in the transport direction.

3. The device according to claim 1, further comprising at least one fork-type sensor configured to measure the continuous web.

4. The device according to claim 1, wherein the measuring ranges of the at least two microwave resonators overlap each other in a transverse direction.

5. The device according to claim 1, wherein the spacing between two absorbent bodies in the transport direction is less than a respective diameter of the at least two microwave resonators, and wherein a signal minima of the shift of the resonance frequency and the spreading of the resonance frequency are evaluated instead of an empty adjustment.

6. A method for measuring absorbent hygiene products, the method comprising:
   spacing absorbent bodies apart from each other along a continuous web;
   moving the continuous web through at least two microwave resonators; and
   determining at least one of a moisture and a density of the absorbent bodies using the at least two microwave resonators, wherein the at least two microwave resonators are configured to continuously measure values of a shift of a resonance frequency and a spreading of a resonance frequency,
   wherein the at least two microwave resonators are positioned at an offset with respect to each other in a transverse and transport direction relative to a direction of transport of the continuous web in order to measure the width of the continuous web, and
   wherein each of the at least two microwave resonators further comprises a measuring range with a homogeneous field distribution, and wherein the at least two microwave resonators are positioned transverse to the transport direction such that the continuous web is covered by the measuring range with a homogeneous field distribution.

7. The method according to claim 6, wherein averaged measured values of the shift of the resonance frequency and the spreading of the resonance frequency of each of the at least two microwave resonators are corrected by an offset of the at least two microwave resonators in the transport direction.

8. The method according to claim 6, wherein the density of each of the absorbent bodies is determined by a sum of the measured values of the shift of the resonance frequency and the spreading of the resonance frequency.

9. The method according to claim 6, wherein the moisture of each of the absorbent bodies is determined by a sum of the measured values of the shift of the resonance frequency and the spreading of the resonance frequency.

10. The method according to claim 8, wherein the sum of the measured values of the shift of the resonance frequency and the spreading of the resonance frequency is divided by a number of summands.

11. The method according to claim 6, wherein the measuring ranges of the microwave resonators overlap each other in a transverse direction.

12. The method according to claim 6, wherein the spacing between two absorbent bodies in the transport direction is less than a respective diameter of the at least two microwave resonators, and wherein signal minima of the microwaves are evaluated instead of an empty adjustment.

* * * * *